US00PP17252P2

(12) United States Plant Patent
Jonkers

(10) Patent No.: US PP17,252 P2
(45) Date of Patent: Nov. 28, 2006

(54) ***DIASCIA* PLANT NAMED 'DALA REEDA'**

(50) Latin Name: *Diascia barberae*
Varietal Denomination: Dala Reeda

(75) Inventor: Johanna B. Jonkers, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/269,174

(22) Filed: Nov. 8, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP14,466 P2 * 1/2004 Stemkens ..... Plt./263
PP16,306 P2 * 3/2006 Schrader ..... Plt./263

OTHER PUBLICATIONS

UPOV ROM GTITM Computer Database, GTI Jouve Retrieval Software 2005/05 Citations for 'Dala Reeda'.*

* cited by examiner

*Primary Examiner*—Wendy Haas
(74) *Attorney, Agent, or Firm*—Jondle & Associates P.C.

(57) ABSTRACT

A new *Diascia* plant particularly distinguished by its medium to large red flowers, deep green foliage, compact and well-branched growth habit, rounded and tight plant habit with upright to narrow spreading branches and early flowering is disclosed.

1 Drawing Sheet

Genus and species: *Diascia barberae.*
Variety denomination: 'Dala Reeda'.

BACKGROUND OF THE NEW PLANT

The present invention comprises a new and distinct cultivar of *Diascia,* botanically known as *Diascia barberae,* and hereinafter referred to by the cultivar name 'Dala Reeda'. The new cultivar originated from a hybridization made in 2003 in Andijk, The Netherlands. The female parent is a proprietary *Diascia* plant designated 'DSZ-39-6' (unpatented), having a deep rose flower color and the male parent is a proprietary *Diascia* plant designated 'DSZ-41-3' (unpatented), having a lilac-rose flower color. The seeds produced by the hybridization were sown in May 2003, and the resulting seedlings were selected in July 2003. A single plant selection was chosen for further evaluation and for asexual propagation in the fall of 2003.

The new cultivar was created in 2003 in Andijk, The Netherlands and has been asexually reproduced repeatedly by vegetative cuttings and tissue culture micropropagation in Andijk, The Netherlands over a two-year period. The plant has also been trialed at Gilroy, Calif. The present invention has been found to retain its distinctive characteristics through successive asexual propagations.

Plant Breeder's Rights for this cultivar were applied for in Europe on Jan. 24, 2005 and in Canada on Mar. 31, 2005.

SUMMARY OF THE INVENTION

The following are the most outstanding and distinguishing characteristics of this new cultivar when grown under normal horticultural practices in Gilroy, Calif. and Andijk, The Netherlands.

1. Medium to large red flowers;
2. Deep green foliage;

3. Relatively compact and well-branched growth habit;
4. A rounded and tight plant habit with upright to spreading branches; and
5. Relatively early flowering.

DESCRIPTION OF PHOTOGRAPH

This new *Diascia* plant is illustrated by the accompanying photograph which shows blooms, buds, and foliage of the plant in full color; the colors shown are as true as can be reasonably obtained by conventional photographic procedures. The photograph is of three 6-month-old plants grown in a greenhouse with natural light in a spring trial setting.

The accompanying photograph shows blooms, buds, mature foliage, and plant habit; the inset shows buds and mature inflorescences and buds.

DESCRIPTION OF THE NEW CULTIVAR

The following detailed descriptions set forth the distinctive characteristics of 'Dala Reeda'. The data which define these characteristics were collected from asexual reproductions carried out in Hillscheid, Germany. The plant history was taken on seven-month-old plants grown in 35-cm-diameter baskets (capable of holding 5-liters of soil and three plants each) in an outdoor trial field under poly-cover rain protection. Color readings were taken under natural light. Color references are primarily to The R.H.S. Colour Chart of The Royal Horticultural Society of London (R.H.S.) (2001 edition). Texture description details were observed under a magnifying glass.

DESCRIPTION OF THE NEW PLANT

Classification:
*Family.*—Scrophulariaceae.
*Botanical name.*—*Diascia barberae* Hook.

Parentage:

*Female parent.*—'DSZ-39-6' a proprietary deep rose *Diascia* plant (unpatented).

*Male parent.*—'DSZ-41-3' a proprietary lilac-rose *Diascia* plant (unpatented).

Growth:

*Form and growth habit.*—Upright with branches ascending and somewhat outwardly spreading to semi-trailing; freely branching and relatively compact.

*Height.*—20 cm (from top of soil) for 7-month-old plants to 35 cm (total vertical height) of a plant in a hanging basket.

*Width.*—65 cm for a 7-month-old plant.

*Spread* (*including flowers*).—54 cm, from the base of the main stem to the tips of the branches.

*Time to produce a finished flowering plant.*—10–11 weeks for a 5-inch pot.

*Outdoor plant performance.*—Plant in full sun; is free-flowering through the summer; has some heat tolerance; use in mixed container planting or mass planting in a bed.

*Time to initiate and develop roots.*—About 20 days in the spring.

*Root description.*—Fibrous and freely branching.

Leaves:

*Arrangement.*—Single and opposite.

*Shape.*—Deltoid to cordate.

*Apex.*—Acute to obtuse.

*Base.*—Truncate to weakly cordate.

*Margin.*—Weakly serrate.

*Texture.*—Glabrous and slightly glossy.

*Immature.*—Color: Upper surface: RHS 137D to RHS 143A. Lower surface: RHS 138B.

*Mature* (*fully expanded*).—Length: 1.6–2.1 cm. Width: 1.4–1.6 cm. Color: Upper surface: RHS 137A to RHS 137B. Lower surface: RHS 138B.

*Venation.*—Type: Pinnate. Color: RHS 144A to RHS 144B.

*Petiole.*—Length: 0.2–0.3 cm. Width: 0.2 cm. Color: RHS 144A.

Stems:

*Length:* 35–40 cm without the inflorescence.

*Diameter.*—0.3 cm as measured in the middle (is square not round).

*Internode length.*—2.0–2.5 cm.

*Color.*—RHS 143B.

*Texture.*—Smooth and glabrous.

*Anthocyanin.*—Absent.

Flower bud:

*Shape.*—Globular and somewhat flattened.

*Diameter.*—0.6 cm.

*Length.*—0.4 cm.

*Color* (*at tight bud*).—RHS N57D (pink).

Inflorescence:

*Inflorescence type.*—Terminal raceme with flowers in an alternate arrangement.

*Blooming habit.*—Fairly continuous.

*Quantity of inflorescences per plant.*—80.

*Lastingness of individual blooms on the plant.*—3–4 days.

*Fragrance.*—None.

*Inflorescence length.*—About 9–10 cm.

*Penduncle.*—Color: RHS 143A. Length: 9.0–9.5 cm. Diameter: 0.2 cm or less. Texture: Covered with fine hair.

Flower:

*Type.*—Single, zygomorphic; fused at the base; 5-lobed.

*Quantity* (*per raceme*).—18–20 flowers and buds at various stages of development; usually 6–7 open flowers at the same time.

*Shape.*—Salver-shaped.

*Diameter.*—2.1 cm.

*Depth.*—0.5 cm.

*Color.*—Upper surface: Between RHS 46D and RHS 53C. Lower surface: RHS 53D. Corolla (inside color): RHS 46A; upper petals have a patch of RHS 13A (yellow) at the base.

*Petals* (*lobes*).—Quantity: 5. Arrangement: Two upper lobes (mainly fused) with two lateral lobes and one lower lobe. Apex: Rounded. Base: Fused. Margin: Entire. Texture: Smooth, papillose.

*Upper lobes, size.*—Length (from the Corolla opening): 0.4–0.5 cm. Width: 0.9–1.0 cm.

*Lateral lobes, size.*—Length (from the Corolla opening): 0.6 cm. Width: 0.7 cm. Spur: Shape: Funnel-shaped and directed downwards. Length: 0.7 cm. Diameter: 0.3 cm. Color: RHS 60D.

*Lower lobe.*—Length (from the Corolla opening): 1.1–1.2 cm. Width: 1.6–1.7 cm.

*Sepals.*—Quantity: 5. Color: RHS 141A. Length: 0.2 cm. Width: 0.1 cm. Shape: Deltoid to lanceolate. Apex: Acute. Base: Fused. Anthocyanin: Absent. Texture: Somewhat rough and pubescent.

*Pedicels.*—Color: RHS 146C. Length: 1.3–1.5 cm. Diameter: 0.1 cm. Texture: Pubescent (very fine).

Reproductive organs:

*Stamens.*—Quantity: 4; coherent, arching towards and somewhat twisting around the pistil. Filament: Color: RHS 187A (nearly black). Length: 0.3 cm. Diameter: 0.1 cm. Anther color: RHS 14D (light yellow). Pollen amount: Abundant. Pollen color: RHS 13A (yellow).

*Pistils.*—Quantity: 1. Length: 0.3–0.4 cm. Stigma color: RHS 143D. Style color: RHS 145C.

Fruit and seed set: Has not been observed.

Disease and insect resistance: Has not been observed.

COMPARISON WITH PARENTAL AND COMMERCIAL CULTIVARS

'Dala Reeda' differs from the female parent, proprietary *Diascia* plant 'DSZ-39-6' (unpatented), in that 'Dala Reeda' has a red flower color while 'DSZ-39-6' has a deep rose flower color. The leaves of 'Dala Reeda' are differently shaped than the leaves of 'DSZ-39-6' . Additionally, 'Dala Reeda' has a more vigorous growth habit than 'DSZ-39-6'.

'Dala Reeda' differs from the male parent, proprietary *Diascia* plant 'DSZ-41-3' (unpatented), in that 'Dala Reeda' has red flowers while 'DSZ-41-3' has lilac-rose flowers. Additionally, 'Dala Reeda' is somewhat taller and has a more upright plant habit than 'DSZ-41-3'.

'Dala Reeda' differs from the commercial cultivar 'Diastonia' (U.S. Plant Pat. No. 14,466) in that 'Dala Reeda' has larger flowers, a more compact plant habit, and flowers earlier than 'Diastonia'.

I claim:

1. A new and distinct cultivar of *Diascia* plant as shown and described herein.

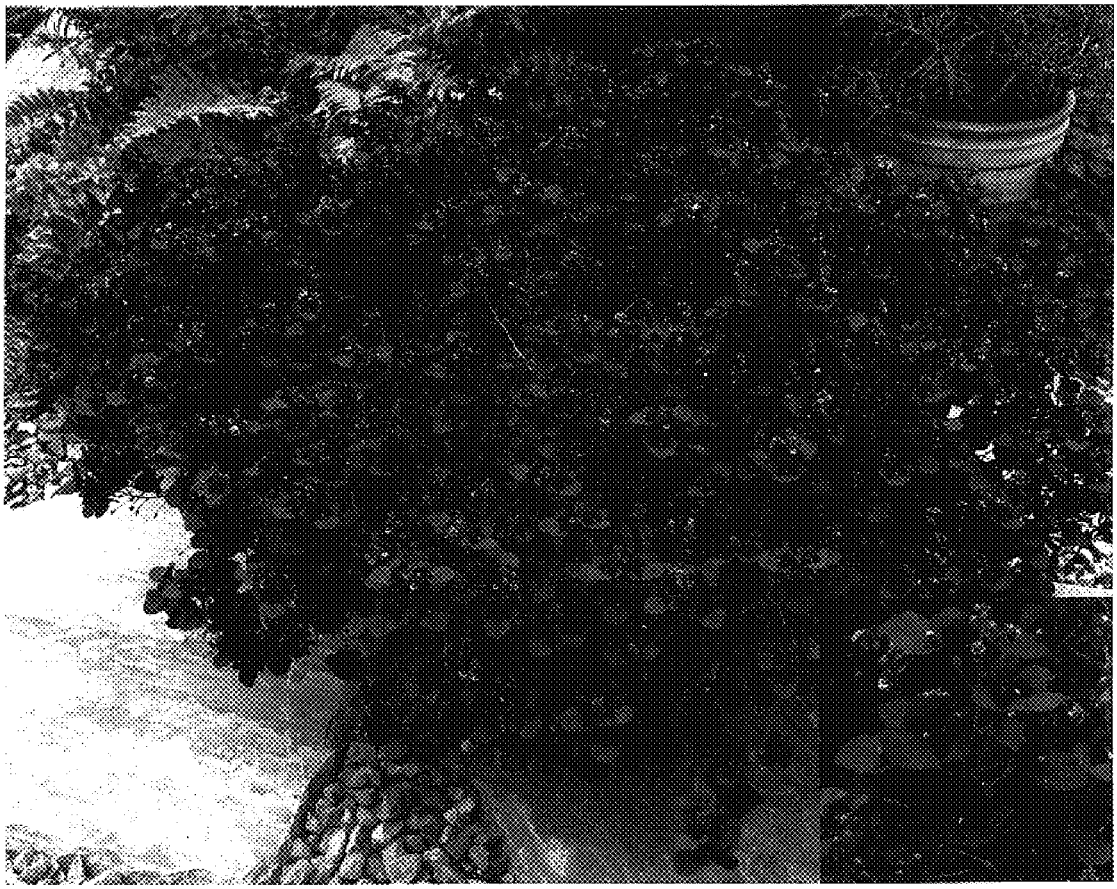

* * * * *